US007443156B2

(12) United States Patent
Hoelzl et al.

(10) Patent No.: US 7,443,156 B2

(45) Date of Patent: Oct. 28, 2008

(54) APPARATUS AND METHOD FOR IDENTIFYING DEFECTS ON OBJECTS OR FOR LOCATING OBJECTS

(75) Inventors: Roland Hoelzl, Munich (DE); Michael Hermann, Villingen-Schwenningen (DE)

(73) Assignee: Pruftechnik Dieter Busch AG, Ismaning (DE)

( * ) Notice: Subject to any disclaimer, the term of this patent is extended or adjusted under 35 U.S.C. 154(b) by 245 days.

(21) Appl. No.: 10/595,897

(22) PCT Filed: Jul. 18, 2005

(86) PCT No.: PCT/DE2005/001273

§ 371 (c)(1), (2), (4) Date: May 18, 2006

(87) PCT Pub. No.: WO2006/007832

PCT Pub. Date: Jan. 26, 2006

(65) Prior Publication Data

US 2007/0242758 A1 Oct. 18, 2007

(30) Foreign Application Priority Data

| | | |
|---|---|---|
| Jul. 19, 2004 | (DE) | 10 2004 034 881 |
| Aug. 12, 2004 | (DE) | 10 2004 039 348 |
| Aug. 23, 2004 | (DE) | 10 2004 040 860 |
| Oct. 21, 2004 | (DE) | 10 2004 051 506 |
| Oct. 25, 2004 | (DE) | 10 2004 051 949 |

(51) Int. Cl.
*G01R 31/28* (2006.01)

(52) U.S. Cl. .................... 324/158.1; 324/238

(58) Field of Classification Search ................. 324/225, 324/158.1, 237, 232, 332
See application file for complete search history.

(56) References Cited

U.S. PATENT DOCUMENTS

| | | | | |
|---|---|---|---|---|
| 3,848,182 | A * | 11/1974 | Gerner et al. | 324/233 |
| 4,110,679 | A * | 8/1978 | Payne | 324/329 |
| 4,230,987 | A * | 10/1980 | Mordwinkin | 324/236 |
| 4,322,683 | A * | 3/1982 | Vieira et al. | 324/225 |
| 4,486,713 | A * | 12/1984 | Gifford | 324/329 |
| 4,675,880 | A * | 6/1987 | Davarian | 375/261 |
| 4,700,139 | A * | 10/1987 | Podhrasky | 324/329 |
| 4,755,753 | A * | 7/1988 | Chern | 324/237 |
| 4,942,360 | A * | 7/1990 | Candy | 324/329 |
| 5,027,069 | A * | 6/1991 | Roehrlein | 324/248 |
| 5,525,907 | A * | 6/1996 | Frazier | 324/334 |
| 5,537,041 | A * | 7/1996 | Candy | 324/329 |
| 5,541,552 | A * | 7/1996 | Suzuki et al. | 329/307 |
| 5,786,696 | A * | 7/1998 | Weaver et al. | 324/329 |
| 6,583,625 | B1 * | 6/2003 | Castle | 324/329 |
| 6,798,197 | B2 | 9/2004 | Lopez | |
| 2005/0109110 | A1 | 5/2005 | Staszewski | |
| 2007/0080681 | A1 * | 4/2007 | Hoelzl et al. | 324/240 |

* cited by examiner

*Primary Examiner*—Ha Nguyen
*Assistant Examiner*—Richard Isla Rodas
(74) *Attorney, Agent, or Firm*—David S. Safran

(57) ABSTRACT

Apparatus and associated method for identifying defects on objects provide for—under computer driving—the AC voltage energization of at least one transmitting coil to be simultaneously effected by a carrier signal, and for an essentially amplitude-modulated received signal to be received by means of at least one receiving coil; what is carried out, furthermore, is a demodulation not only of the carrier signal contained in the received signal by means of magnitude and phase formation, but also a demodulation of the harmonics of the carrier which are contained in the received signal, likewise by means of respectively associated magnitude and phase formation, to be precise preferably by using a Fourier or wavelet transformation method.

8 Claims, 11 Drawing Sheets

15 13 V 12 L1 L2 14 A/D 17 KF & PA 42 18' 16 GEN. 48' 32 TRIG. 33 44 TIMER Signal processor FREQU. TRANSF. DIGIFILTER 40 60'; 60'' 60 62 DISP. KEYB. 70 LAN 50

13
V
D
15
L2
L1
(e.g. 100 kHz)
$U_{out}$
$U_{in}$
14
12

$u_{IN}$
$t/T$
1.0
0.8
0.6
0.4
0.2
0
-0.2
-0.4
-0.6
-0.8
-1.0
0
1e3
2e3
3e3
4e3
5e3
6e3
A
B
C
D
E
F
G
H
I
J
K
L
M
N
O

APPARATUS AND METHOD FOR IDENTIFYING DEFECTS ON OBJECTS OR FOR LOCATING OBJECTS

BACKGROUND OF THE INVENTION

1. Field of the Invention

The present invention relates to an apparatus and a method which are suitable for locating metallic objects e.g., in the ground, and can also be used for identifying defects on objects. In particular, the invention can be used for identifying defects or faults on metallic objects, and here in particular, on ferromagnetic semifinished or finished products.

2. Description of Related Art

Similar apparatus and methods of this type have been known for a relatively long time; however, the problem still exists of providing higher-quality portable measuring instruments of the generic type, in particular, those based on an eddy current measurement technique, or based on an ultrasonic measurement technique or related measurement techniques.

SUMMARY OF THE INVENTION

Thus, a primary object of the present invention is to provide a device of the generic type for which the outlay required for its production is significantly reduced, and which simultaneously enables more precise and more reliable measurements—as far as possible in conjunction with a reduced energy requirement.

The indicated object is achieved, in accordance with the present invention, with the aid of computer driving, by the AC voltage energization of at least one transmitting coil being simultaneously effected by a carrier signal, an essentially amplitude- and/or phase-modulated received signal being received by means of at least one receiving coil, and a demodulation of the received signal being formed using the computer and a Fourier or wavelet transformation method, in such a way that a predefined number of digitally determined measurement results (samples) are fed to such a transformation method, an associated magnitude value and/or phase value is calculated for the frequency of the carrier signal and such a magnitude and/or phase value is used as a direct measure of a present signal strength or phase angle of the demodulated received signal.

According to an alternative embodiment, the transformation method is used to calculate a spectrum, associated magnitude values and/or phase values being calculated for the frequencies of the carrier signal and at least one further frequency component of the spectrum, and the magnitude and/or phase values thus calculated are used as a direct measurement of a present signal strength vector or phase angle vector of the demodulated received signal.

One important aspect of the invention is based on the insight that it is possible to use hitherto unused signal sources, either by themselves, or in interaction with signal sources that are known per se and used according to the prior art.

Specifically, the invention additionally provides, inter alia, the following either individually or in combination:

- a method according to the above embodiments, in which temporally successive Fourier or wavelet transformations are carried out which are based on sets of, in each case, at least 3, but preferably at least 9, progressively determined measured values (samples)
- a method according to the above embodiments, in which sequences of temporally mutually superposed or temporally overlapping sample sets are used, so that overlapping Fourier or wavelet transformations can also be carried out;
- a method according to the above embodiments, in which at least 2 samples are detected and processed per full wave of the carrier signal;
- a method according to the above embodiments, in which less than 1 sample is detected and processed per full wave of the carrier signal, and accordingly, an intermittent data acquisition in the sense of an undersampling is effected;
- a method according to the above embodiments, provision being made of an additional digitally acting filter method for the signal to be demodulated and/or the harmonics thereof;
- a method according to the above embodiments, provision being made of an additional digitally acting filter method for the demodulated signal or the demodulated signal vector;
- a method according to the above embodiments, in which a digital low-pass filter effect takes place or is provided for the demodulated signal and the width of the mathematically assigned digital low-pass filter is made variable by virtue of a differently sized number of digitally determined measured values (samples) being fed to a respective Fourier or wavelet transformation, so that a small number of samples effects a larger filter width and a larger number of samples effects a smaller filter width of the mathematically assigned digital low-pass filter for the demodulated signal;
- a method according to the above embodiments, in which the number of samples is chosen to be inversely proportional to the frequency of a frequency signal output by a speed sensor, or is directly proportional to the pulse lengths output by said sensor;
- an apparatus for carrying out a method according to the above embodiments, having devices at least in the form of a transmitting coil, at least one receiving coil, at least one electronic computing unit, at least one analog-to-digital converter, and one or more housing(s) enclosing these devices;
- the use of the apparatus, or of a method, according to the above embodiments in industry, to be precise for the nondestructive identification of faults on semi-finished or finished products;
- the use of the apparatus according to the above embodiments for the localization of metallic objects in the ground, or under or in water.

The procedure according to the invention provides, for these purposes, an extended demodulation method which is regarded as innovative and differs considerably from a simple rectification method and also significantly from conventional synchronous demodulation methods. Moreover, the demodulation method may, in this connection, also be used for the evaluation of a greatly reduced subset of the available information. Independently of this, it may be combined with an innovative adaptive filter method.

The demodulation method according to the invention may essentially be interpreted as one for amplitude-modulated signals. Such signals are known to occur in conventional radio/broadcast signals. However, the demodulation method is also readily able to identify phase changes on a signal to be demodulated and may then be interpreted as a phase demodulation method.

As is preferably provided according to the invention, these demodulation methods may also be used in the context of, e.g., eddy current, EMAT or ultrasonic testing on industrially produced test specimens. In this respect, the demodulation process according to the invention presupposes the existence of a carrier, at least the ability to recover said carrier from associated signal sources. Conventional demodulation methods of the type employed in materials testing are restricted merely to determining the spectral energy density, and if appropriate, the phase angle in the vicinity of the carrier frequency, in particular, that of the adjacent sidebands which typically carry the temporally varying information of interest. By contrast, the invention provides for additionally determining, if appropriate, also the energy densities (viz. amplitudes) and/or phase information in the vicinity of at least double, if necessary also triple and, if appropriate, also quadruple the frequency in comparison with the carrier frequency, generally of those harmonics whose signal/noise ratio is greater than one. Moreover, for control purposes, the energy density of a DC component (having the frequency zero) can readily be determined by the method according to the invention.

The demodulation operation according to the invention for signals for the purpose of materials testing thus provides for, in contrast to conventional demodulation methods, carrying out of a discrete Fourier transformation, or wavelet transformation or the like, on the basis of a selectable present number of measured values that are determined digitally and temporally progressively. An amplitude or intensity of the carrier (that is to say of the carrier signal) that is presently determined, in this way, in the signal received by the receiving coil, possibly also in proximity to the carrier, then produces a first present demodulation value. A first present phase value can simultaneously be calculated in this way. The same applies to the abovementioned energy densities or amplitudes and/or phase values of analyzable harmonics.

In other words, the invention involves taking into account not only the temporal variation of the amplitude or of the phase angle of the carrier, but preferably also the temporal variation of the amplitude or of the phase angle of said harmonics, to be precise individually or in combination with one another. Consequently, in comparison with known methods, a plurality of amplitude and/or phase values are provided which, according to the invention, depending on the application, can be evaluated in additive/subtractive combination(s), or furthermore, also other characteristic values which can be obtained by means of multiplication or division of the original values by one another. It is noted at this juncture that a conventional, e.g., synchronous demodulation signal merely provides amplitude and phase information in the region of the carrier frequency components shifted to a frequency value "zero" (principle of synchronous demodulation). A simultaneous provision of such information for higher frequencies (that is to say harmonics associated with the carrier) is not possible, in principle, by means of conventional synchronous demodulation (cf. FIGS. 8 & 9).

Thus, the method according to the invention is based on the fact that, under appropriate preconditions, not only the information content of the carrier and its proximity can be exhausted and utilized, but likewise and in addition, also the information content of the harmonics of the carrier, to be precise with respect to their temporally variable amplitudes and/or phase angles. If some harmonics of the carrier prove to be temporally constant, this fact can be utilized for comparison and reference purposes. Anticipatory reference is made here to FIG. 2, which reproduces the spectrum of an eddy current test signal that was generated by means of a commercial test system on a test specimen having a plurality of defects. Based on approximately 1.5 million measured values (=samples) sampled consecutively and equidistantly with 16-bit resolution, which proportionally also comprise the signal components caused by defects, it is clearly shown in semi-logarithmic Fourier-transformed representation that such a signal also has, besides the intensive carrier signal (having an intensity of approximately 92 dB), the first, second and third harmonics and also further spectral lines which are at a significant distance from the so-called noise (here approximately 0 dB). In addition, the intensity of the DC voltage component (=frequency at 0 kHz) contained in the signal mixture can be read. Such information, more precisely: the variation of such information over time, can be utilized innovatively according to the invention.

The invention is explained below with reference to the accompanying drawings.

DETAILED DESCRIPTION OF THE INVENTION

Figure 1:
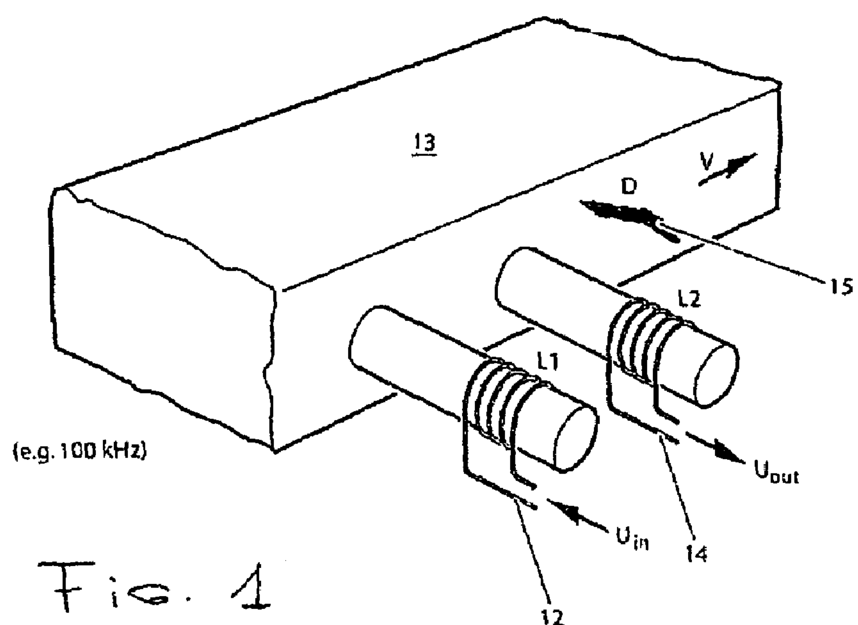
FIG. 1 is a schematic diagram of the measurement principle generally used.

FIG. 1 schematically shows part of a test specimen 13, represented in the form of an industrial semi-finished product (slab), together with a defect 15 that is present there and is to be detected. The test specimen 13 can move—in a manner known per se—at constant or varying speed parameter "v") past a test station containing at least one transmitting coil 12 (L1) and at least one receiving coil 14 (L2). The at least one transmitting coil 12 is energized suitably in accordance with the concept of the invention, by means of an essentially constant AC voltage (approximately 1-1200 kHz; if appropriate, also special frequencies). An eddy current signal is tapped off as a received signal at the at least one receiving coil 14. This signal is of the same frequency as the transmitting AC voltage, but may have temporal amplitude fluctuations and/or phase fluctuations caused by on or more defects 15 (cf, FIG. 13 with a single region of reduced amplitude and, if appropriate, altered phase).

Figure 2:
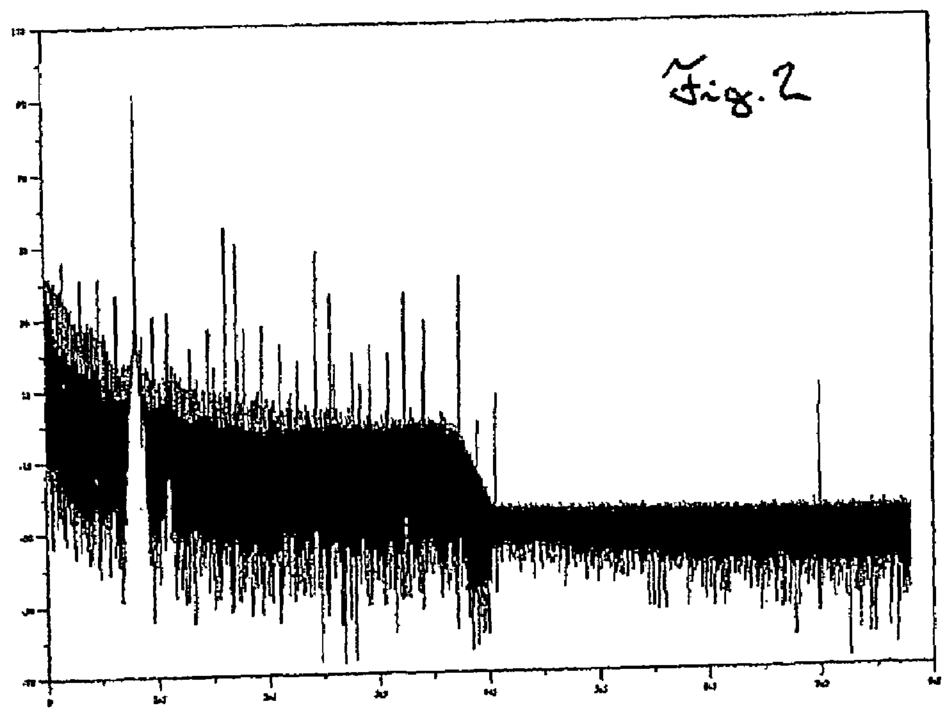
FIG. 2 is a plot of averaged spectral components (PSD) of an obtained measurement signal.

The spectral component ("PSD") of a signal which is obtained in such a way and converted by means of Fourier transformation is shown in a semi-logarithmic representation in FIG. 2. The narrowband line of maximum intensity is to be assigned to the so-called carrier, which in this case has a frequency of 5,000 kHz. As is evident, the DC component at the frequency 0.0 kHz is significantly lower, and even lower than the intensity of the so-called first and second harmonics (that is to say at 10 kHz and 15 kHz, respectively). Besides the last-mentioned spectral components, diverse further lines are present which are distinctly demarcated from a base level encountered at approximately 0 dB. This figure reproduces the frequency spectrum which is based on a very large number of progressively digitally sampled measured values (samples) and which contains signal components which are essentially both attributed to defect-free regions of the test specimen examined but also comprise those signal components which are attributable to some defect regions (four of these in this case) of the test specimen. It is again emphasized that the method according to the invention, in contrast to other demodulation methods that have been used heretofore, can determine not only the temporal variation of the carrier, but additionally the magnitude and temporal variation of a possibly superposed DC voltage component, so that an additional measured value can be evaluated and supervised.

Figure 3:
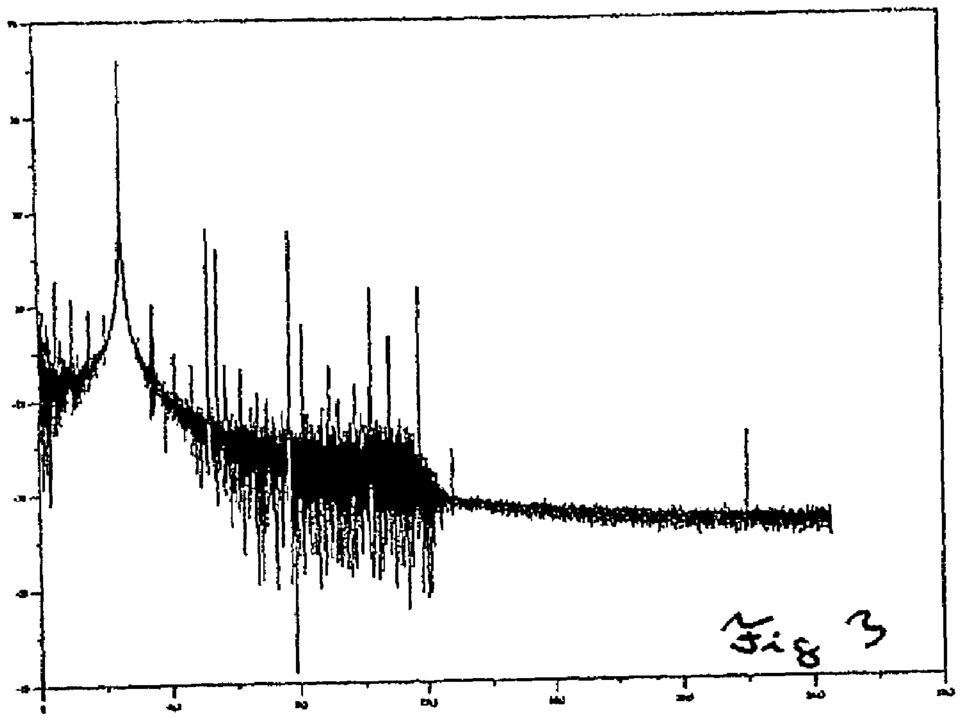
FIG. 3 is a plot of spectral components in the absence of faults.

FIG. 3 represents a similar circumstance to FIG. 2, but based on a reduced, progressively recorded number of samples from the set of the abovementioned samples which are attributed to defect-free regions of the test specimen examined. The proportional spectral lines appear to be widened on account of the reduced number of samples (only approximately 50,000) in comparison with FIG. 2. The spectral line for the carrier frequency represents, according to the invention, a signal to be demodulated, both the intensity and the phase angle of this signal being of interest. As is already evident here in FIG. 3, the ratio of the intensities of the first harmonic to the carrier line and also that of the first harmonic to the second harmonic has changed markedly in comparison with FIG. 2.

Figure 4:
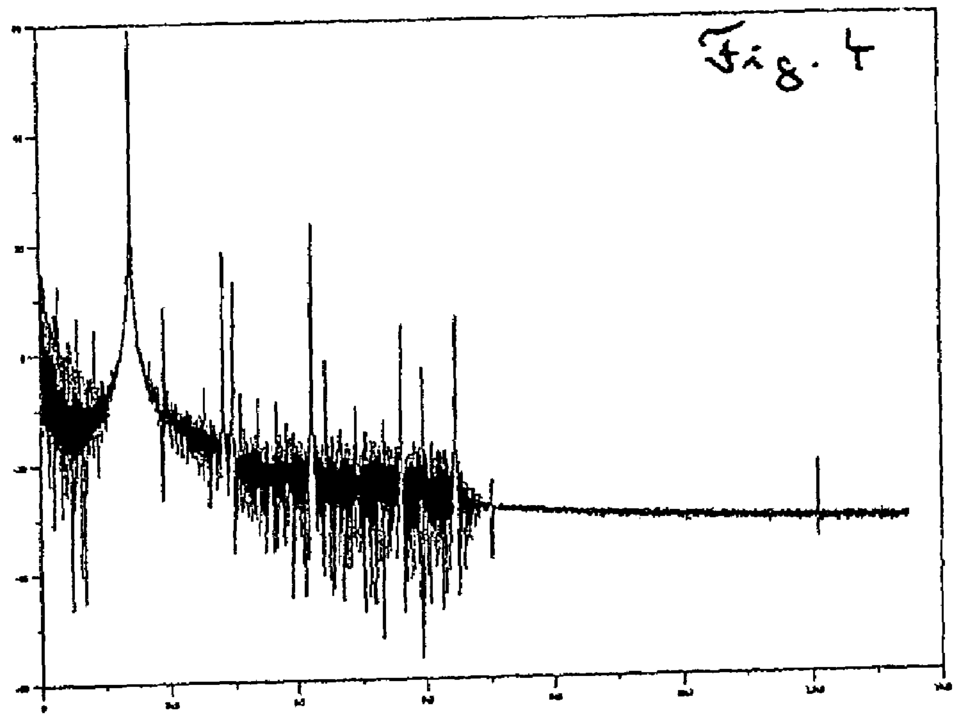
FIG. 4 is a plot of spectral components in the presence of a fault.

FIG. 4 represents a similar circumstance to FIG. 2, likewise based on a reduced number of samples (approximately 30,000) from the set of the abovementioned samples which are attributed here, however, to an individual defective region of the test specimen examined. The proportional spectral lines likewise appear to be widened, and it becomes clear that the ratio of the intensities of the carrier line, first harmonic and second harmonic, thus the intensities of a signal vector provided by demodulation, has once again changed.

Figure 5:
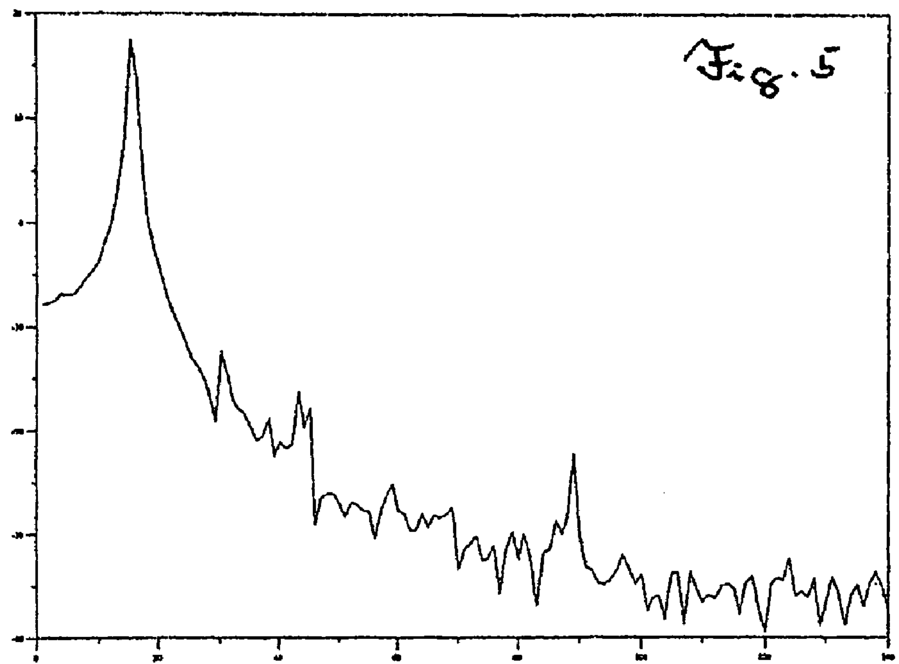
FIG. 5 is a plot of spectral components in the absence of faults, with intermittent sampling.

FIG. 5 is comparable to with FIG. 3, but is based on another important aspect of the invention, namely, according to which a comparable representation can be obtained with a significantly reduced outlay on hardware and software if measured values are acquired (sampled) intermittently. In other words, the same signal was not evaluated on the basis of consecutively acquired measured values, but rather only on the basis of a drastically reduced subset of samples. By way of example, only every 97th sample was evaluated in the case shown. As is evident, this results in an information content that is comparable with FIG. 3, albeit reduced.

Figure 6:
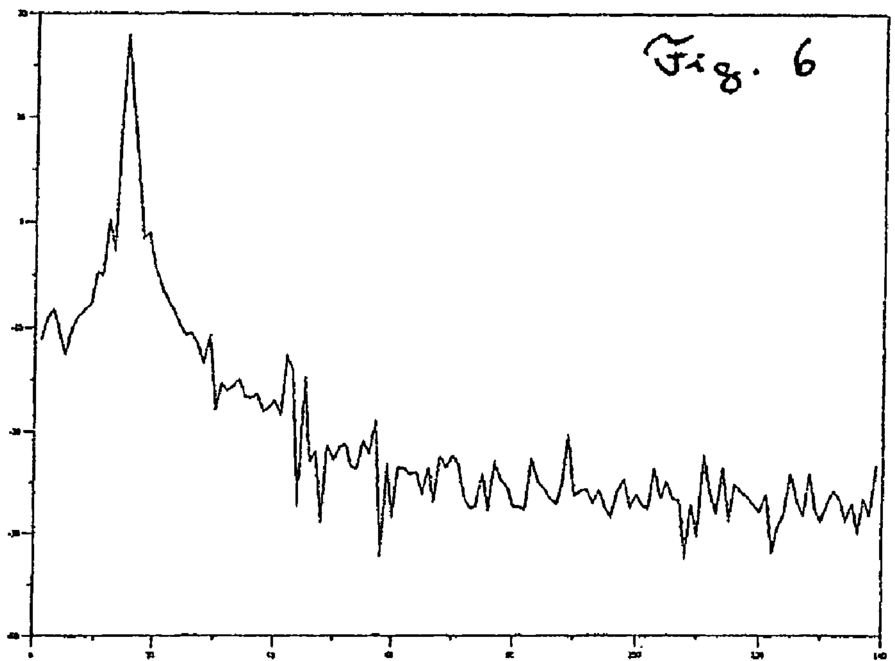
FIG. 6 is a plot of spectral components in the presence of a fault, with intermittent sampling.

A similar situation applies to FIG. 6, which is comparable to with FIG. 4, that is to say is based on a likewise reduced number of samples. These are attributed here, however, in a directly comparable manner, to an individual defective region of the test specimen examined. In this case, too, only every 97th sample was progressively used for the signal representation of the demodulated signal. The intensities of the first and second harmonics can be seen besides the carrier line.

Figure 7:
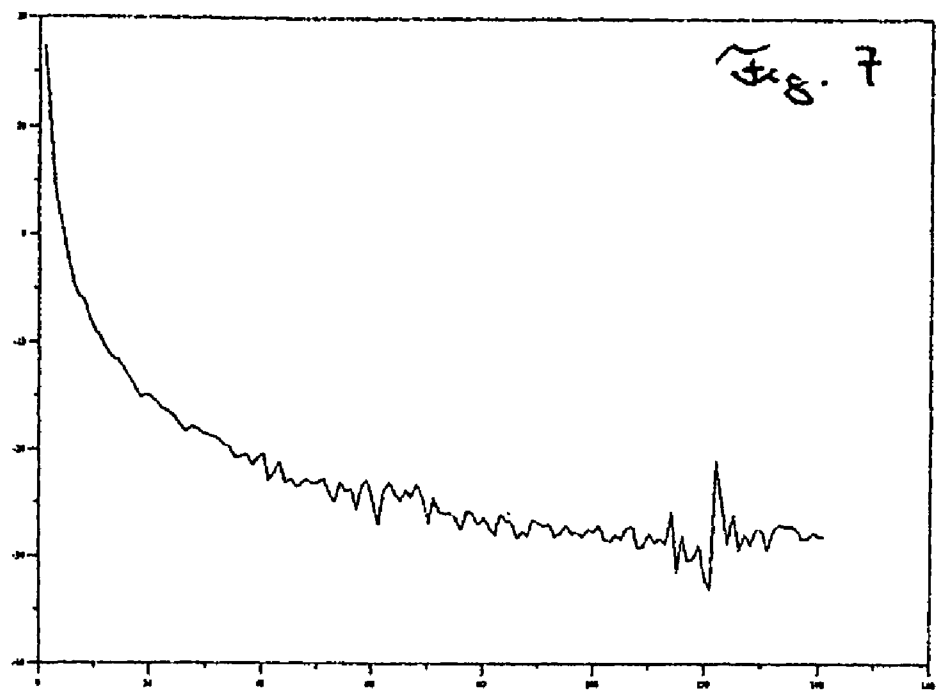
FIG. 7 is a plot of spectral components in the case of synchronous demodulation, with intermittent sampling, in the absence of faults.

In contrast thereto, FIG. 7, which is comparable to FIG. 3 or FIG. 5, that is to say is likewise based on a further reduced number of samples, shows the following: in the case of a synchronous demodulation which operates with sine and cosine values in pairs and which is based in a comparable manner on progressively and/or intermittently selected samples (here, however, every 96th sample is acquired), the carrier line is merely converted into a DC voltage component (with a time-variable character). Information on any harmonics or the originally present DC component of the signal is no longer present for mathematical reasons, irrespective of whether or not a signal caused by a defect is present.

Figure 8:
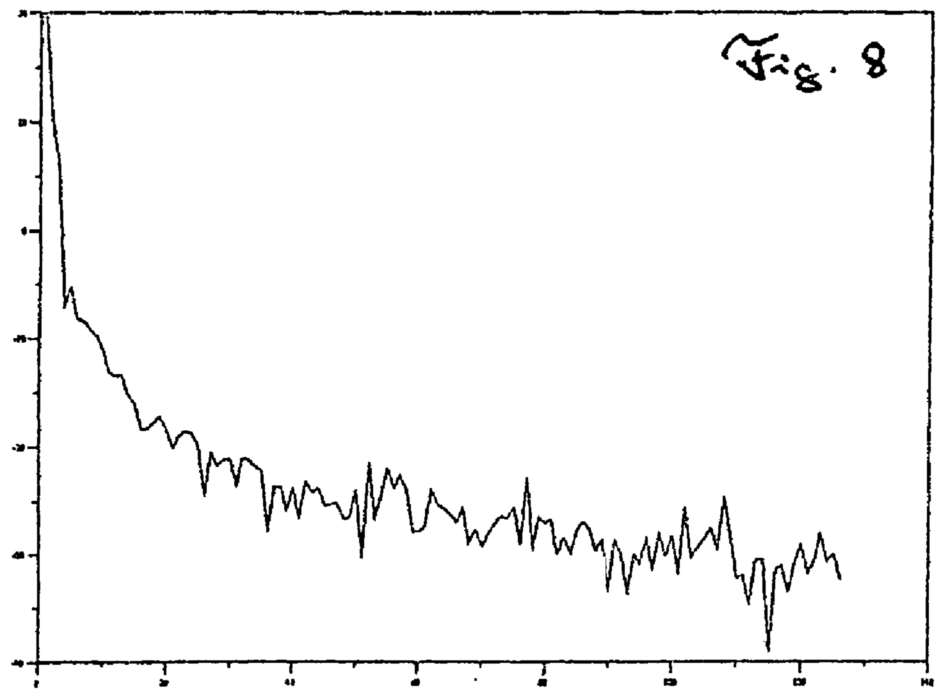
FIG. 8 is a plot of spectral components in the case of synchronous demodulation, with intermittent sampling, in the presence of a fault.

The counterexample is shown in FIG. 8, which is also based on progressively but intermittently selected samples (likewise only every 96th sample), but which are attributed to a signal range that is representative of the defect or material damage already shown in FIGS. 4 and 6. Besides the currently present DC voltage component (at the frequency 0 kHz), no further spectral lines that can be evaluated are present.

Figure 9:
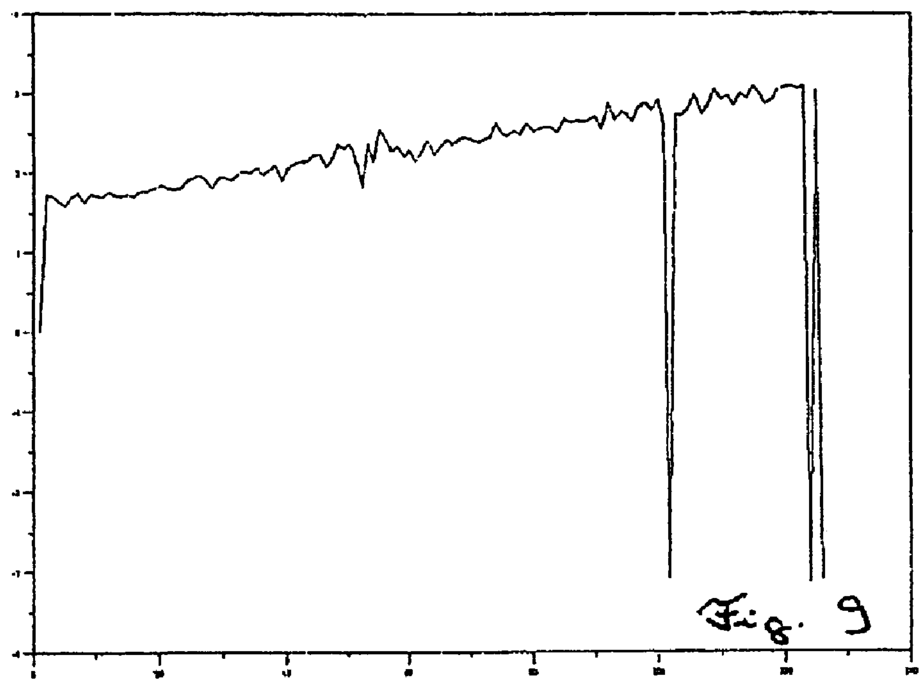
FIG. 9 is a plot of the phase behavior in the case of synchronous demodulation, with intermittent sampling, in the absence of faults.
Figure 10:
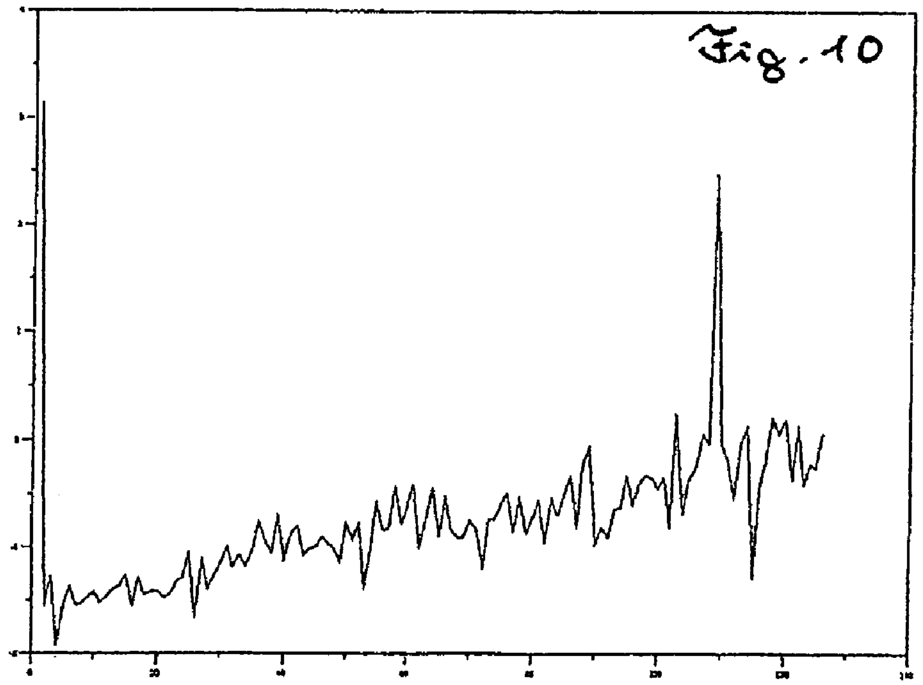
FIG. 10 is a plot of the phase behavior in the case of synchronous demodulation, with intermittent sampling, in the presence of a fault

The phase information based on a synchronous demodulation which is associated with FIGS. 7 and 8 is then shown in FIGS. 9 and 10, respectively, but this is of little use. All that is represented is that the phase differences of the spectral components appear to have less variance when a defect is absent than when a defect is presently observed.

Figure 11:
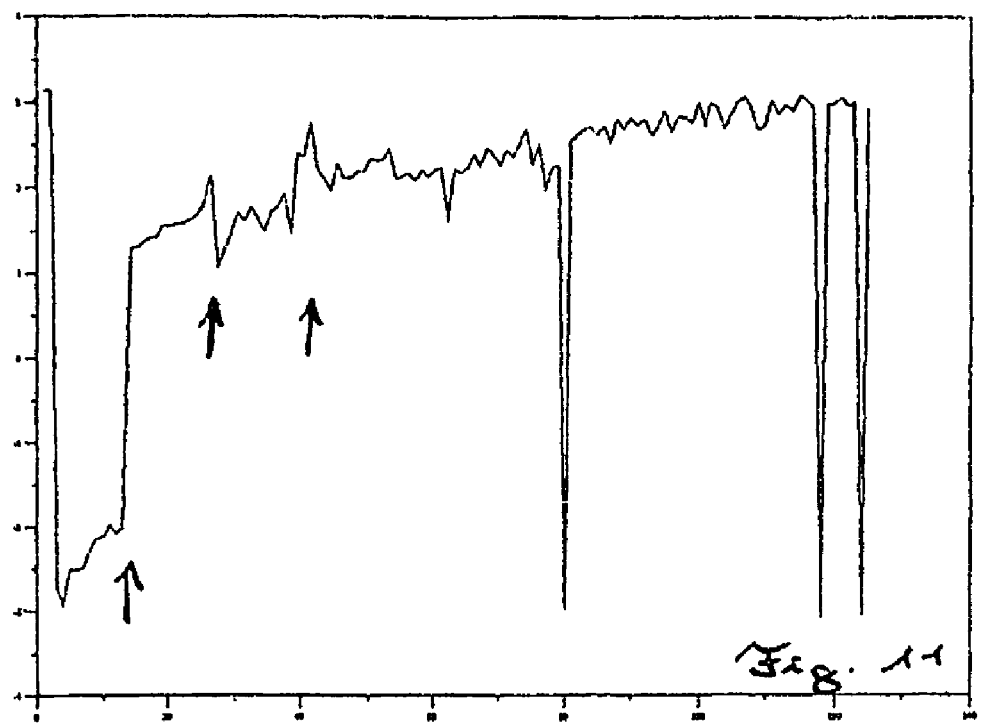
FIG. 11 is a plot of the phase behavior in the case of Fourier demodulation, with intermittent sampling, in the absence of faults.

As can be seen from FIG. 11, the method according to the invention affords usable advantages here by virtue of the fact that, besides the phase information for the carrier, it is additionally possible to represent specifically that information for the first and second harmonics (cf. the indicating arrows depicted in the figure). This applies to "intermittent" data acquisition, too, which here is again based on, for example, every 97th sample of a signal used, to be precise when the test specimen is free of defects. (In practice, the detection of unused samples will understandably be dispensed with and then, at a greatly reduced sample frequency, only those samples will be detected which originate from the subsection mentioned as an example, based on every 97th sample.—This procedure makes it possible, inter alia, to use slow, high-resolution or simply just cost-effective analog-digital converters, and furthermore, advantageously reduces the required computational complexity).

Figure 12:
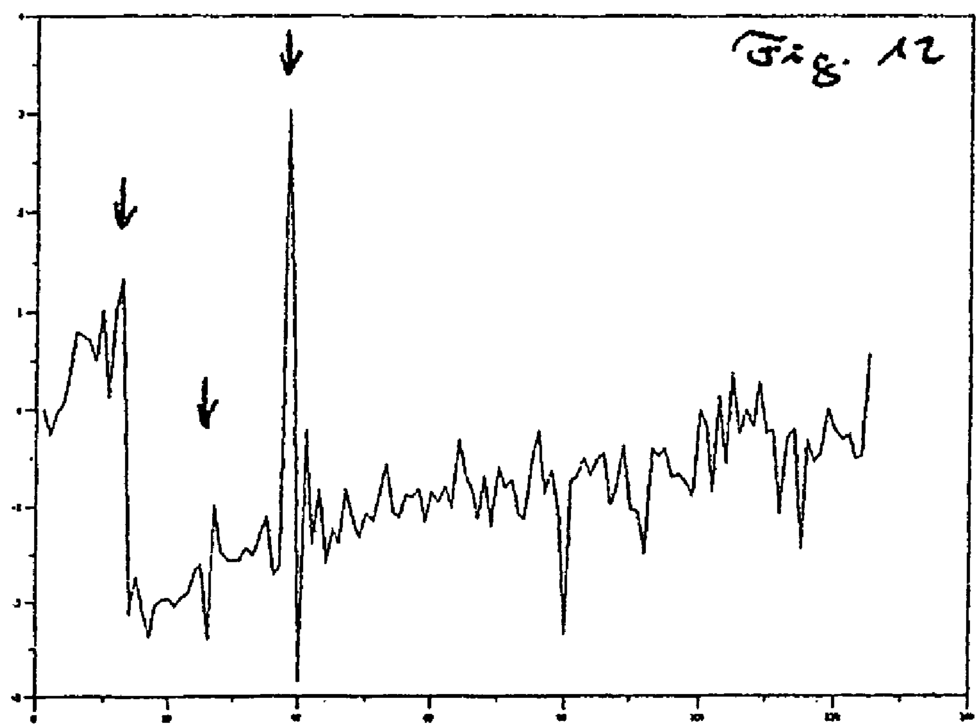
FIG. 12 is a plot of the phase behavior in the case of Fourier demodulation, intermittent sampling, in the presence of a fault.

By contrast, compared to FIG. 11, FIG. 12 shows the conditions if the test specimen has a defect. The overall phase shift shown is insignificant and is to be assigned to a start phase value. What is important above all is that a very significant item of phase information of the second harmonic can be discerned besides the phase angle of the carrier; to an extent, a similar item in the vicinity of the first harmonic (cf. the arrows depicted in the figure) can be seen as well. It is one of the principal matters of the invention to also use precisely this phase information in a novel way (that is to say specifically also for the alternative "intermittent" mode of operation, that is to say in the manner of undersampling with distinctly less than one sample per fault wave of the carrier) for improved detection of defects on objects. In the same way, this phase information can be used for improved detection of objects by battery-operated so-called metal detectors. In this case, the "intermittent" data acquisition and mode of operation with undersampling enables a very welcome saving of energy.

When evaluating data acquired consecutively (that is to say without temporal gaps), it is expedient to use standard Fourier transformations (e.g., by FFT or by DFT) or else, if appropriate, wavelet transformation. A first filter effect is produced in a manner known per se in that the spectral lines represented by Fourier transformation have a width that is inversely proportional to the number of samples taken as a basis (indeterminacy principle). In this respect, it is beneficial according to the invention to feed no fewer than, in each case, 9 suitable samples to a Fourier transformation in order that, besides the carrier line information (which represents a present demodulation intensity value and the phase reference thereof), at least the first and second harmonics can also be represented according to their magnitude (intensity) and phase. In this way, additional demodulation results are obtained for two or more further frequencies in parallel and without additional outlay on hardware.

Figure 13:
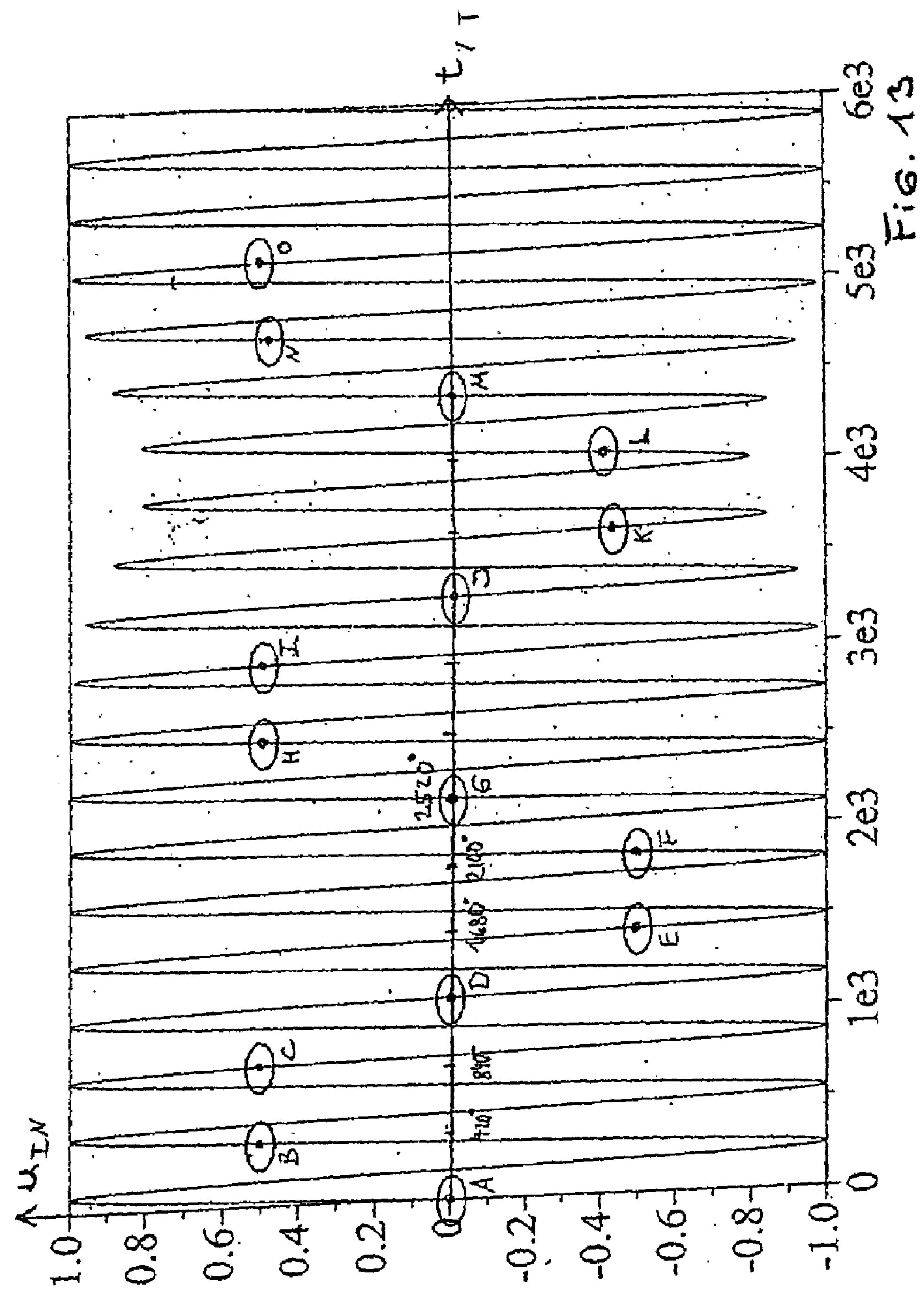
FIG. 13 is a plot of an amplitude-modulated time signal.

FIG. 13 shows a schematic diagram—which is merely an example—of the procedure when applying the data acquisition operating intermittently (preferably equidistantly intermittently). It is assumed—as shown—that a carrier voltage "$U_{IN}$" having a sinusoidal profile over the time "t" or an associated angular dimension "ϕ" is detected by coil L2. The carrier voltage is modified for a short time (cf. time measure 4*e*3) in the presence of a fault and then rises to the original value again.

As illustrated, it is possible to carry out a data acquisition at the times A, B, C, D, E, F, G, H, I, J, K, L, M, N, O, in particular, using an interconnection of a so-called A/D converter and a sample-and-hold element. As shown, it is assumed that the acquisition takes place at a time interval corresponding to 420° el. of the carrier, that is to say in the manner of an undersampling at 0°, 420°, 840°, 1260° el. etc. In a manner known per se, this gives rise to a mapping both of the carrier voltage and of the modulation effect, cf. instants K and L, which have a lower voltage value than at the comparable instants E and F. As likewise known per se, not only the intensity conditions, but also the associated phase conditions are mapped. In this respect, a Fourier transformation which processes, e.g., the nine voltage values present at C D E F G H I J K reproduces not only an average amplitude value for the fundamental but also the phase angle thereof with respect to a reference phase. For this purpose, it is necessary, if appropriate, in a known manner to correctly take account of the start phase angle of the respective first sample to be transformed. The section-by-section detection of Fourier transforms can thus be carried out by blocks of, e.g., each 9 (or significantly more) samples which are produced by/after shifting by defined angular increments, viz. number of samples. The person skilled in the art is in this case familiar with methods that permit the computational complexity for determining results section by section to be kept low, e.g., by FFT in the case of 8 or 16 samples taken as a basis per block.

As already mentioned, a signal detection operating intermittently or in undersampling fashion makes it possible not only to save considerably on hardware costs for the associated electronics, but also to drastically reduce the required computational complexity. In FIGS. 5 to 12, already mentioned, this is, e.g., a factor of approximately 100, which, without the assistance of measuring instruments, the untrained user will notice immediately and positively.

It must be emphasized that the demodulation results obtained in the manner portrayed are obtained for the purpose of materials testing for, e.g., four frequencies including the frequency 0.0 kHz merely by means of a single computational method, namely, e.g., by spectral analysis by means of discrete Fourier transformation, and in this case, requires just a single analog/digital converter for the purpose of signal conversion. However, the invention does not preclude providing two or more analog/digital converters which operate independently of one another and which are triggered progressively, for the purpose of an increased data throughput. The last-mentioned solution makes it possible to provide A/D converters that operate relatively slowly, and nevertheless to implement rapid data acquisition. As mentioned, said computational method may particularly advantageously be based on the analysis of measurement data that have been obtained in the manner of an undersampling, in particular a temporally equidistant undersampling.

The component parts of an overall system according to the invention are described below with reference to the drawing of FIG. 14.

Figure 14:
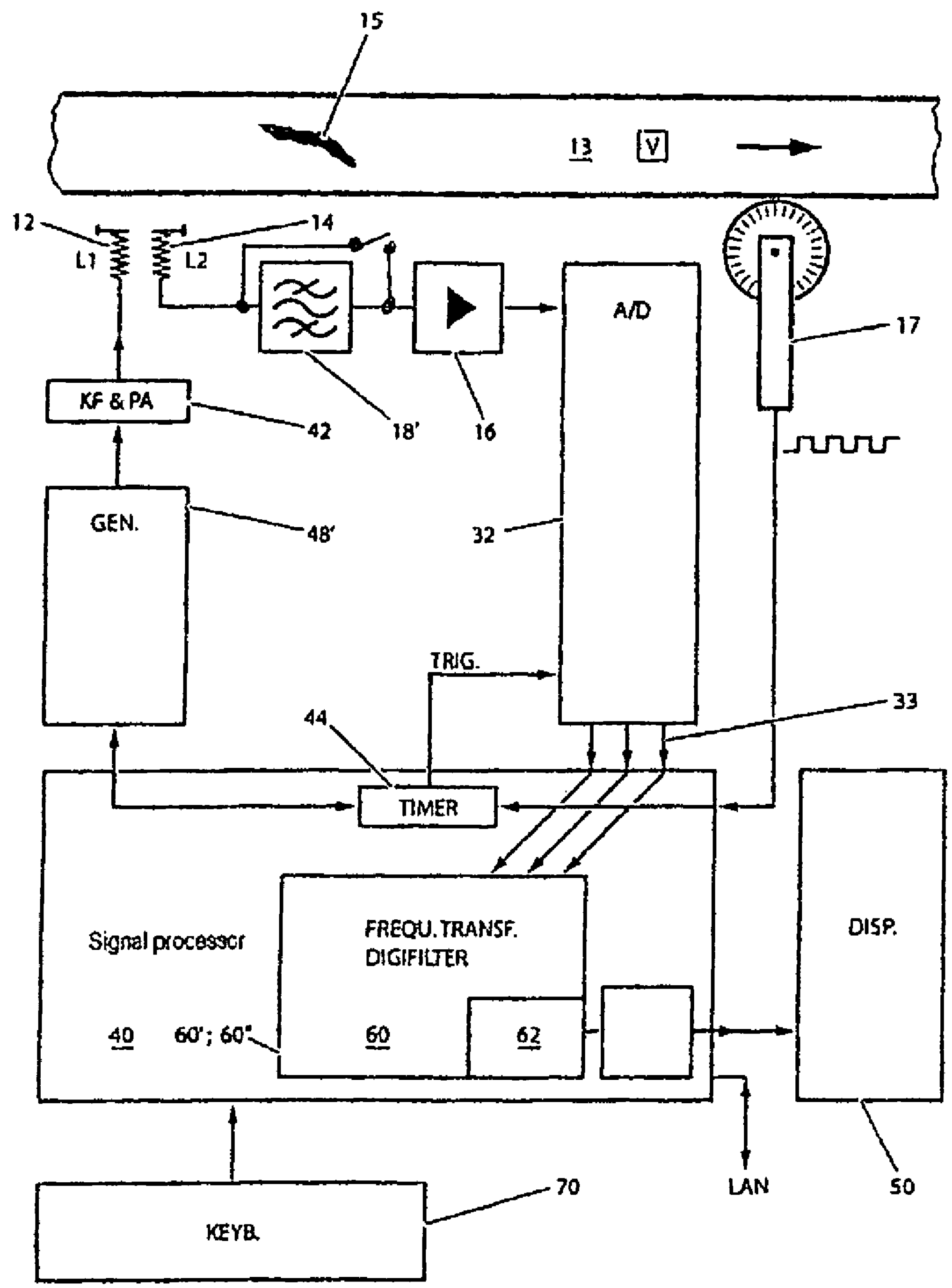
FIG. 14 is a schematic diagram of an overall system according to the invention.

The upper part of FIG. 14 schematically shows a test specimen 13 in the form of an industrial semifinished product (slab) together with a defect 15 to be detected. The test specimen 13 can move at varying speeds (parameter "v") past a test station containing at least one transmitting coil 12 (symbol: L1) and at least one receiving coil 14 (symbol: L2). The speed of the test specimen is detected by an electronically acting speed pick-up 17, which permits corresponding electronic signals to be output.

Besides a high-resolution A/D converter 32 according to the latest technology, an electronic unit or computer 40 having the properties of a signal processor is an essential hardware component of the invention. A counter/timer module 44 may be provided separate from the computer 40 or may be integrated into the latter. The subsystem 60 contains the device—required according to the invention—for generating Fourier transforms (alternatively or equivalently: wavelet transforms) and an apparatus—referred to as a digital filter unit—with filter sets 62 defined in terms of software. These are likewise preferably integrated in the computer 40 and may be implemented in dedicated hardware or, in cost-saving fashion, merely in software that can be executed in the computer. In a manner that is technically customary per se, the computer 40 can be linked externally to a keyboard 60, a display 50 and/or to a local area network (reference symbol "LAN") or WAN.

Even in the stationary, that is to say unmoving, state of the test specimen 13, the timer 44 generates a time signal having a high frequency stability. The frequency of this time signal can be varied as desired or according to the technical requirements and this time signal is typically available as a square-wave signal such as is known per se for a timer. The square-wave signal is supplied to a generator 48' with a predefined frequency. The generator 48' generates from this either a square-wave signal or a sinusoidal signal, preferably with an adjustable amplitude. (A square-wave signal has, in a manner known per se, odd-numbered harmonics that can advantageously be used here). The generated signal is passed to an optionally provided curve shaper KF and a power amplifier PA, which may be combined in a unit 42. The power amplifier is suitable for energizing the transmitting coil 12. Consequently, an eddy current field is induced in the test specimen 13 in a manner known per se. The eddy current field is registered by the schematically shown receiving coil 14—which may also be formed, according to the prior art, as a differential coil set or the like—and is fed as an AC voltage to the AID converter 32 already mentioned, if appropriate via one or more bandpass filters 18', and preferably, via at least one (preferably adjustable) preamplifier 16. The A/D converter has a resolution of typically 18 bits or better, preferably 22 bits or better. Under specific preconditions (e.g., in low-cost devices), a resolution of 12 bits is also taken into consideration, particularly if approximately 1000 or more samples in each case are fed to a Fourier transformation. The A/D converter 32 is preferably able to carry out much more than 500 analog/digital conversions per second. As known per se, when a defect 15 is present in the test specimen, a modified eddy current field results which induces an AC voltage that is altered in amplitude and/or phase in the receiving coil 14.

The performance of the method according to the invention depends, to a certain extent, on the performance of the A/D converter or A/D converters used. In this case, the resolution thereof (in bits) is also of importance besides the minimum conversion time. Otherwise, according to the invention, there is a considerable configurational possibility with regard to a sampling scheme to be used; that is to say the times at which the signal supplied by the coil L2 is, or is intended, to be evaluated (sampled). Only a number of samples of more than 3, better more than 9, in each case with a different phase angle relative to the zero crossings of the carrier signal is taken as a basis for an individual demodulation operation. This number is limited upwardly only by practical conditions. The manner of providing samples that are to be evaluated set by set in each case can also be effected according to very different schemes. Although a temporally equidistant provision of samples is preferred, this is not absolutely necessary, since, in principle, an analysis according to Lomb (Lomb-Scargle periodogram) can also be performed for the purpose of a demodulation effect according to the invention.

When using Fourier methods, it is expedient to choose and to use the factors (so-called "n-th roots of unity") used as complex numbers in the calculation of an individual set of samples such that the (complex-value) sum of these factors produces the value 0 in a manner known per se. Similar boundary conditions and considerations arise in the equivalent application of wavelet methods. The inherently expedient procedure is not mandatory, however, since it is possible, if appropriate, to have recourse to equivalent computational methods.

The invention may optionally also be combined with an electronically acting speed sensor 17. This option has the particular advantage that, in comparison with devices that are currently commercially available, it is possible to obtain a considerable saving of filter module sets for the purpose of further treatment of the demodulated signal(s) in the manner described below:

If only few samples are used per data set to be evaluated, then spectral components of the signal to be evaluated or demodulated are provided from a larger environment of the carrier frequency, and also the associated harmonics. This is based on the so-called indeterminacy principle. It is known that the environment or the respective line width, and thus, the desired demodulation result is inversely proportional to the number of samples presently used in each case.

In obtaining a high selectivity, that is to say high line sharpness, according to the invention, a large number of samples is to be fed to a calculation (transformation, e.g., DFT, FFT or the like) that is presently to be performed in each case.

Under this precondition, it is possible according the invention to replace, with very little outlay for hardware, the present-day cost-intensive filter stages which carry out an adapted additional treatment of the signal to be evaluated in accordance with a variable test specimen speed.

In this case, it is assumed that, at slow test specimen speeds, usually it is necessary to evaluate only relatively small, that is to say narrow band frequency ranges in the vicinity of the carrier. In conventional synchronous demodulation, this is performed by means of an appropriately set low-pass filter having a small bandwidth. At higher test specimen speeds, it is necessary to evaluate wider and enlarged frequency ranges in the vicinity of the carrier. The situation is vaguely similar to that in the replay of audiotape information, when a slow replay speed of the audio tape is accompanied only by a small signal bandwidth, but a high replay speed is accompanied by a large signal bandwidth.

The abovementioned indeterminacy principle likewise means that the attainable bandwidth is inversely proportional to the available measurement time assuming the normal situation of proportionality between the number of samples and the associated measurement time.

If, accordingly, at a high test specimen speed "v", a large filter bandwidth is desired for the signal to be evaluated, then a small number of samples, that is to say a short (effective) measurement time, is to be chosen. (The effective measurement time may, however, as explained above, be appropriately extended by a suitable intermittent or undersampling operation in order to meet the conditions of an A/D converter or the available computer power).

At a low test specimen speed "v", it is accordingly necessary for a larger number of samples to be taken as a basis for the small desired filter bandwidth sought. According to the invention, this can be achieved with a surprising minimal outlay by choosing the number of samples taken as a basis per transformation to be directly proportional to the pulse length output by the speed sensor.

This sensor may be constructed in a simple manner known per se, e.g., by means of light barriers, such that a slow speed "v" of the test specimen supplies a low frequency speed signal which proportionally acquires a higher frequency as the speed increases. One example might be: a speed of 0.1 in/sec effects pulse lengths of 15,000 microseconds, and a speed of 10 m/sec generates pulse lengths of the speed signal of only 150 microseconds, etc.

Accordingly, it is possible according to the invention now to obtain the desired filter effect on the already demodulated signal by taking the determined pulse length of the speed sensor as an essentially direct measure of the number of samples that are to be evaluated set by set in each case, so that, e.g., approximately only 75 samples are fed to a DFT or FFT in the last-mentioned case and, e.g., approximately 7500 samples in the former case. As is familiar to the person skilled in the art, the computational complexity in calculating Fourier transforms rises only subproportionally for an increasing number of samples, so that a skilful utilization of the computational capacity of the electronics provided can take place in the context according to the invention. It is useful to limit the number of measured values that are to be fed to a transformation in each case; at the very least—when the test specimen is at a standstill—a corresponding item of status information should be supplied by the speed sensor.

Further configurational possibilities arise according to the invention by virtue of the fact that the transmission frequency can also be modified to a certain extent in that it is derived by integer division from a significantly higher-frequency time or frequency base. In particular, it is beneficial to generate a sinusoidal transmission voltage for coil L1 in a manner known per se by means of a software-controlled counter and an assigned digital sine table, whether by means of a D/A converter connected downstream or by means of a timer module connected downstream by means of pulse code modulation. It is more cost-effective, of course, to provide, using purely digital means, only a frequency-variable square-wave voltage, which, as mentioned, has the additional advantage of supplying the harmonics of interest in a significant intensity without additional outlay.

In order to save energy during operation of a measuring instrument according to the invention, the procedure may be such that the transmitting coil is energized only for a few full waves prior to detection of the sample in accordance with a desired transmission signal (in order to realize a transient recovery process) and is de-energized immediately after detection of the sample at an appropriately chosen point in time, a technically advantageous oscillation decay behavior of the transmitting coil being sought. This is advantageous particularly for battery-operated, portable devices.

FIGS. 15 to 18 show some results for visual evaluation as were obtained according to the invention using the information already taken as a basis in FIGS. 3 to 6, 11 and 12, that is to say in particular using the diverse amplitude and phase information. The data of the carrier, of the first harmonic and of the second harmonic are used in multiple relation and concatenation.

Figure 15:
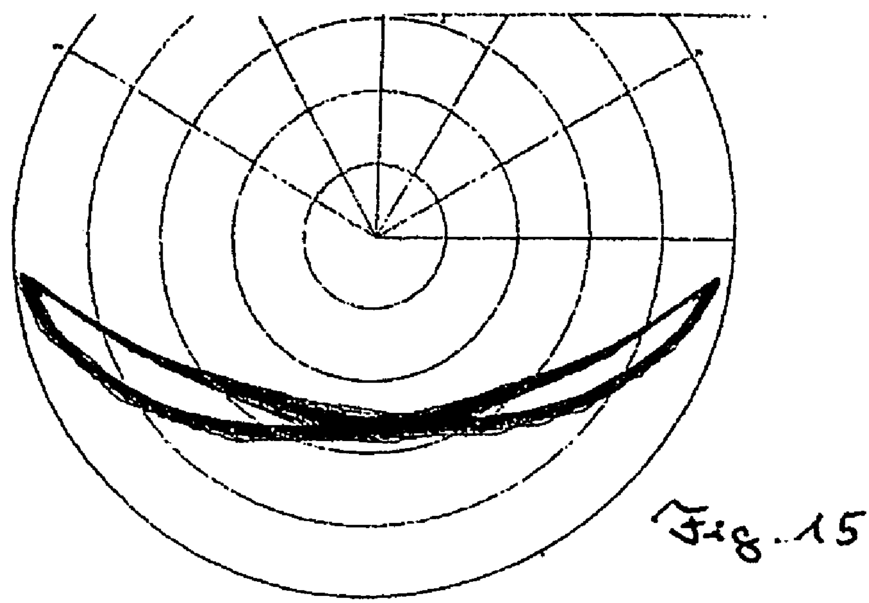
FIG. 15 is an illustration of a result obtained for a Fourier-demodulated overall signal in the absence of faults.

In this case, FIG. 15 is based on the continuous evaluation of Fourier transformations which were carried out on the basis of all those samples that were also used for FIG. 3, that is to say without a test specimen defect, and during a shorter time interval.

Figure 16:
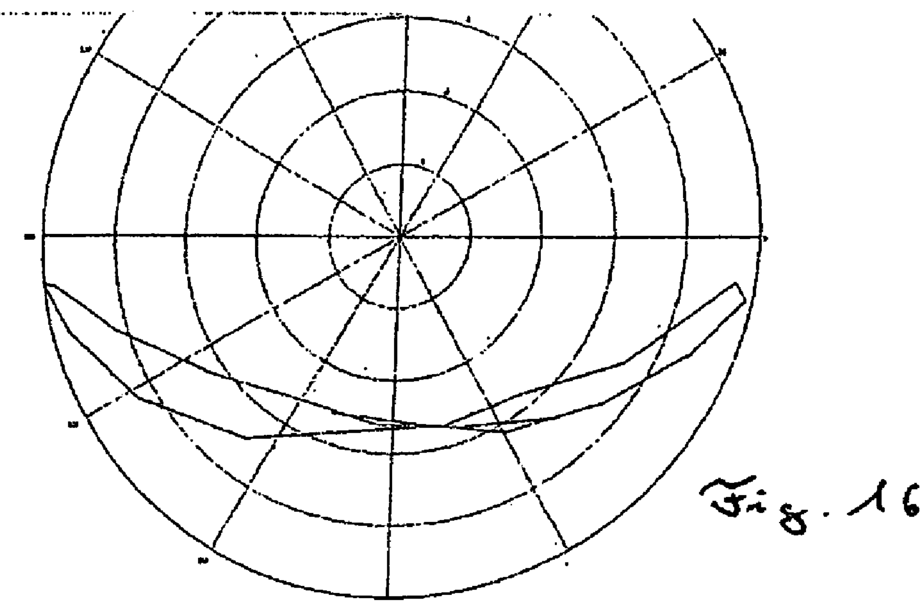
FIG. 16 is an illustration of a result obtained for a Fourier-demodulated signal based on intermittent sampling, in the absence of faults.

FIG. 16 shows a comparable illustration, based on the data also associated with FIGS. 5 and 11 ("intermittent" data acquisition in the manner of undersampling). The signal shape comparable with FIG. 15 and having an approximately crescent-moon-shaped contour, although with a reduced information content, is evident.

Figure 17:
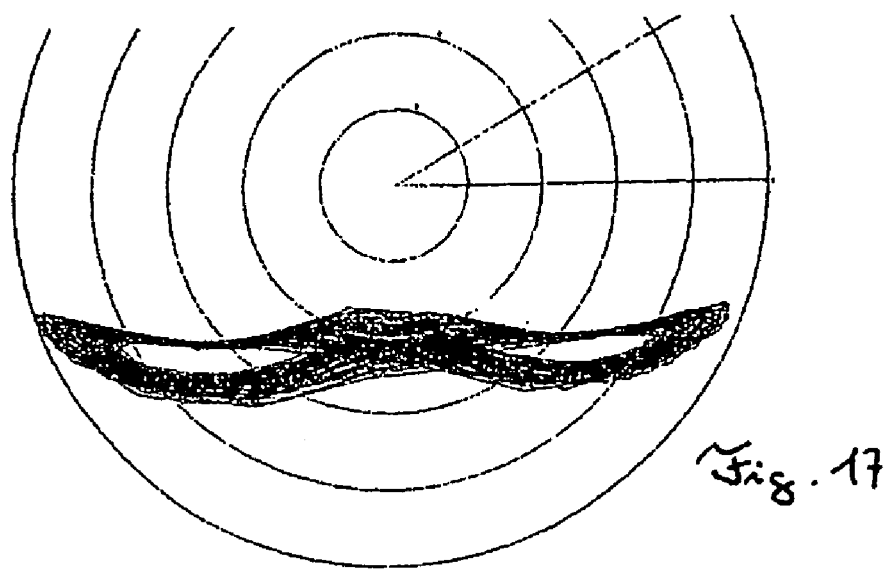
FIG. 17 is an illustration of a Fourier-demodulated overall signal with a fault observed.
Figure 18:
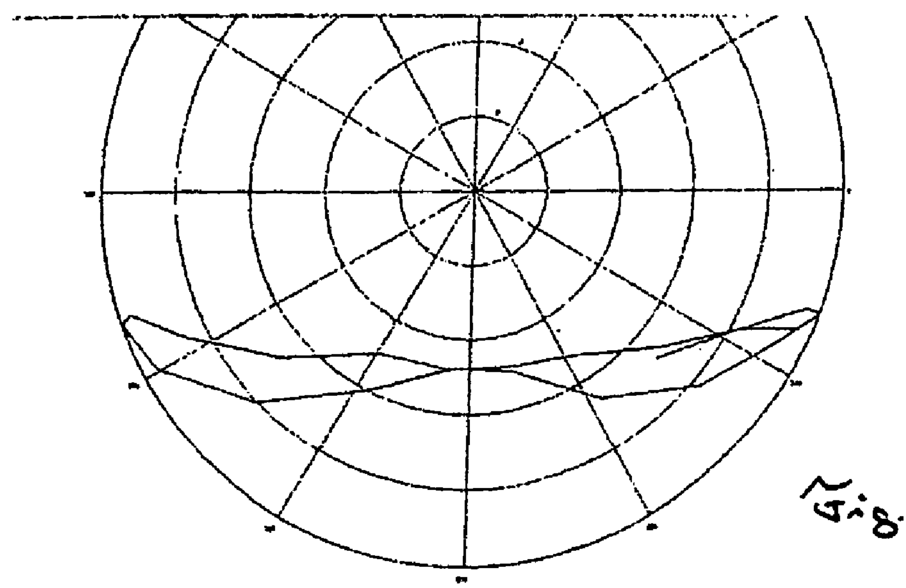
FIG. 18 is an illustration of a result obtained for a Fourier-demodulated signal based on intermittent sampling, with a fault observed.

For comparison, FIGS. 17 and 18 show the case when there is a defective test specimen surface, without and respectively with "intermittent" data acquisition (with chosen distance number equals 97 samples). Now, that is to say in the case of a detected material fault, the envelope of the lines illustrated is of distinctly extended configuration and significantly different than in the case of FIGS. 15 and 16.

Figure 19:
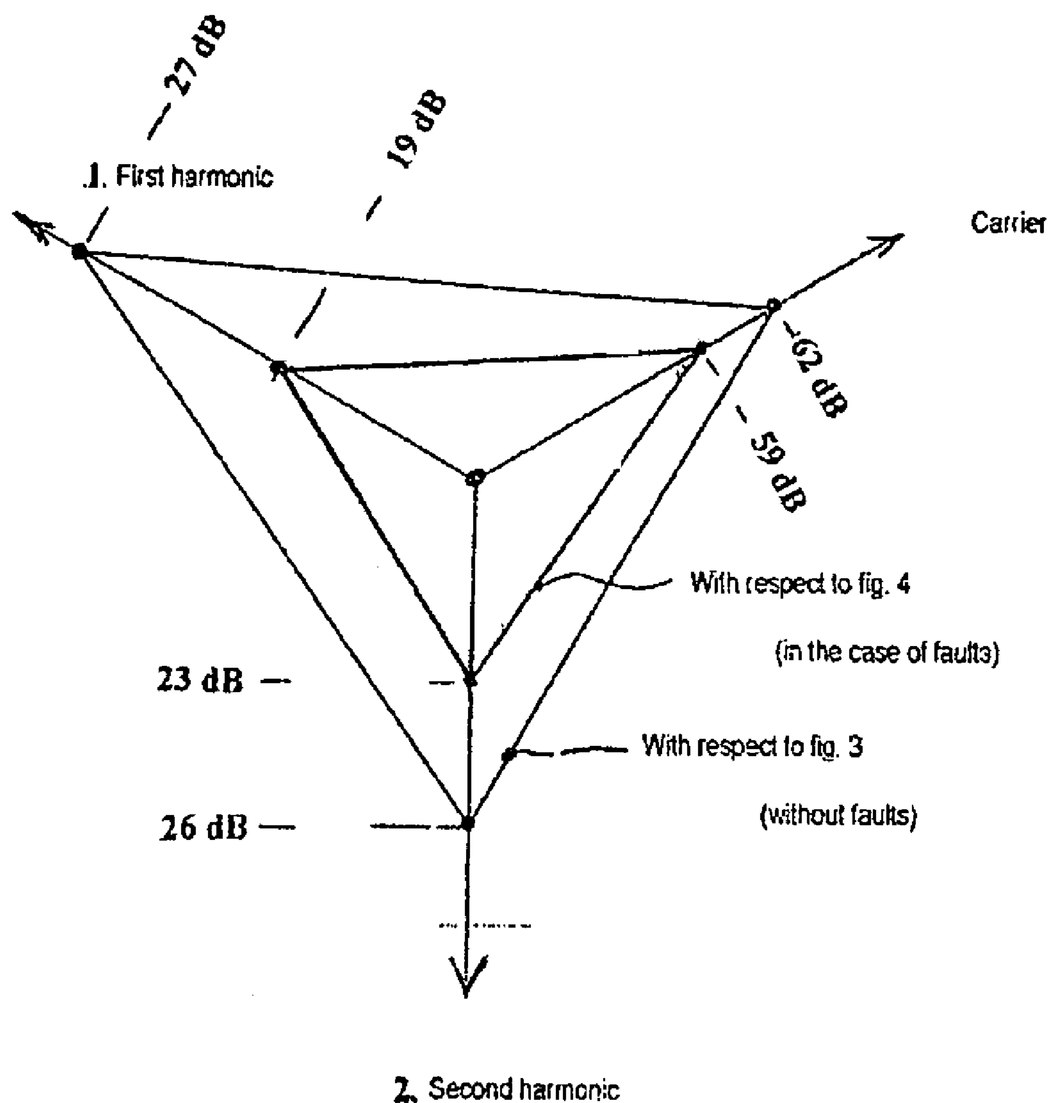
FIG. 19 is an illustration of a comparative result obtained for Fourier-demodulated signals, in the presence and absence of a fault/defect.

Another form of the result illustration is reproduced in FIG. 19. Presently observed values of the intensities by Fourier transformation for carrier, first harmonic and second harmonic are plotted simultaneously in trigonal coordinates or in trilinear coordinates on a suitably scaled logarithmic (that is to say, e.g., decibel) or linear scale. The end points of the plotted values are connected to form a triangle, as shown. FIG. 19, in this case, relates to the corresponding values from FIGS. 3 and 4. As can be seen, even without the likewise possible analysis of the associated phase information, significant differences arise in the forms of the outer triangle, which represents the absence of faults, and the inner triangle, which results when a material fault is present. As can already be gathered from FIGS. 3 and 4, the interesting fact arises that the signals of the first harmonic have a difference of approximately 8 dB, and are thus manifested to a significantly greater extent than the difference for the carrier signal or that of the second harmonic (which, in each case, differ by approximately 3 dB). The logarithmic scale direction chosen remains free to be reversed, so that a triangle in the presence of a fault is represented larger than in the fault-free case.

It goes without saying that FIGS. 15 to 19 are to be understood merely as examples of how acceptance or damage results calculated according to the invention can be visualized. The number of visualization possibilities in comparison with modes of representation known heretofore for test methods of the type under consideration here is comparatively extensive and can be modified in an approximately arbitrary manner on account of the almost completely digital character of the fault identification proposed. It is thus also possible to perform a conventional representation with a correspondingly reduced information content if this is desirable for comparison purposes. Furthermore, it goes without saying that, for an automated fault handling method, the data sets and information obtained according to the invention have to be fed to an expediently suitable pattern recognition device in order to be able to automatically drive external aids, such as fault marking devices, saws, etc. The apparatus and methods according to the invention can be used with highly diverse sensor systems, in particular, ultrasonic and eddy current based sensor systems, but also with so-called EMAT systems, or systems which use so-called magneto-resistive sensors for detecting the eddy current fields.

What is claimed is:

1. A method for locating a metallic object or for identifying defects thereon, comprising the steps of:

energizing at least one transmitting coil with an AC voltage for transmitting a carrier signal to the object and receiving at least one of an essentially amplitude-modulated received signal and phase-modulated received signal resulting from the carrier signal by means of at least one receiving coil, and demodulating the received signal using a computer and a Fourier or wavelet transformation method using a predefined number of digitally determined measurement results, calculating at least one of an associated magnitude value and phase value for the frequency of the carrier signal, and using the calculated at least one of an associated magnitude and phase value as a direct measure of one of a present signal strength and a phase angle of the demodulated received signal;

wherein said demodulating step comprises multiple demodulating of the received signal using the computer and the Fourier or wavelet transformation method; wherein said calculating step also comprises calculating of a spectrum when the at least one of associated magnitude values and phase values are calculated for frequencies of the carrier signal; and wherein at least one additional frequency component of said spectrum is used with the calculated at least one of the magnitude and phase values as said direct measure one of the present signal strength vector and phase angle of the demodulated received signal.

2. The method as claimed in claim 1, wherein temporally successive Fourier or wavelet transformations are carried out based on sets of, in each case, at least 3 progressively determined measured values.

3. The method as claimed in claim 1, wherein temporally successive Fourier or wavelet transformations are carried out based on sets of, in each case, at least 9 progressively determined measured values.

4. The method as claimed in claim 2, wherein sequences of temporally mutually superposed progressively determined measured values are used.

5. The method as claimed in claim 1, wherein at least 2 samples are detected and processed per full wave of the carrier signal.

6. A method for locating a metallic object or for identifying defects thereon, comprising the steps of:

energizing at least one transmitting coil with an AC voltage for transmitting a carrier signal to the object and receiving at least one of an essentially amplitude-modulated received signal and phase-modulated received signal resulting from the carrier signal by means of at least one receiving coil, and demodulating the received signal using a computer and a Fourier or wavelet transformation method using a predefined number of digitally determined measurement results, calculating at least one of an associated magnitude value and phase value for the frequency of the carrier signal, and using the calculated at least one of an associated magnitude and phase value as a direct measure of one of a present signal strength and a phase angle of the demodulated received signal;

wherein intermittent data acquisition is performed with less than 1 sample being detected and processed per full wave of the carrier signal.

7. A method for locating a metallic object or for identifying defects thereon, comprising the steps of:

energizing at least one transmitting coil with an AC voltage for transmitting a carrier signal to the object and receiving at least one of an essentially amplitude-modulated received signal and phase-modulated received signal resulting from the carrier signal by means of at least one receiving coil, and demodulating the received signal using a computer and a Fourier or wavelet transformation method using a predefined number of digitally determined measurement results, calculating at least one of an associated magnitude value and phase value for the frequency of the carrier signal, and using the calculated at least one of an associated magnitude and phase value as a direct measure of one of a present signal strength and a phase angle of the demodulated received signal;

comprising the additional step of digitally filtering at least one of the signal to be demodulated and the harmonics thereof, wherein the digitally filtering is a digital low-pass filtering effect is provided for the demodulated signal using a mathematically assigned digital low-pass filter that has a width that is varied as a function of the number of digitally determined measured values being fed to a respective Fourier or wavelet transformation, so that a small number of measured values effects a larger filter width and a larger number of measured values effects a smaller filter width of the mathematically assigned digital low-pass filter.

8. The method as claimed in claim 7, wherein the speed of the object along the at least one transmitting coil is measured with a speed sensor and the number of digitally determined measurement results is chosen to be one of inversely proportional to the frequency of a frequency signal output by the speed sensor, and directly proportional to pulse lengths output from said speed sensor.

* * * * *